(12) United States Patent
Wegerich

(10) Patent No.: US 8,620,591 B2
(45) Date of Patent: Dec. 31, 2013

(54) MULTIVARIATE RESIDUAL-BASED HEALTH INDEX FOR HUMAN HEALTH MONITORING

(75) Inventor: Stephan W. Wegerich, Geneva, IL (US)

(73) Assignee: Venture Gain LLC, Naperville, IL (US)

( * ) Notice: Subject to any disclaimer, the term of this patent is extended or adjusted under 35 U.S.C. 154(b) by 0 days.

(21) Appl. No.: 12/984,400

(22) Filed: Jan. 4, 2011

(65) Prior Publication Data

US 2011/0172504 A1    Jul. 14, 2011

Related U.S. Application Data

(60) Provisional application No. 61/295,072, filed on Jan. 14, 2010.

(51) Int. Cl.
- G01N 33/48 (2006.01)
- G06G 7/58 (2006.01)
- A61B 5/0205 (2006.01)
- A61B 5/021 (2006.01)

(52) U.S. Cl.
USPC ............................... 702/19; 703/11; 600/301

(58) Field of Classification Search
None
See application file for complete search history.

(56) References Cited

U.S. PATENT DOCUMENTS

| | | |
|---|---|---|
| 4,937,763 A | 6/1990 | Mott |
| 5,009,833 A | 4/1991 | Takeuchi et al. |
| 5,063,513 A | 11/1991 | Shank et al. |
| 5,093,792 A | 3/1992 | Taki et al. |
| 5,109,700 A | 5/1992 | Hicho |
| 5,123,017 A | 6/1992 | Simpkins et al. |
| 5,173,856 A | 12/1992 | Purnell et al. |
| 5,195,046 A | 3/1993 | Gerardi et al. |
| 5,251,285 A | 10/1993 | Inoue et al. |
| 5,255,208 A | 10/1993 | Thakore et al. |
| 5,309,379 A | 5/1994 | Rawlings et al. |
| 5,390,776 A | 2/1995 | Thompson |
| 5,421,204 A | 6/1995 | Svaty, Jr. |
| 5,450,321 A | 9/1995 | Crane |
| 5,463,769 A | 10/1995 | Tate et al. |
| 5,465,321 A | 11/1995 | Smyth |
| 5,473,532 A | 12/1995 | Unno et al. |
| 5,500,940 A | 3/1996 | Skeie |
| 5,502,543 A | 3/1996 | Aboujaoude |
| 5,559,710 A | 9/1996 | Shahraray et al. |
| 5,561,431 A | 10/1996 | Peele et al. |
| 5,586,066 A | 12/1996 | White et al. |
| 5,602,733 A | 2/1997 | Rogers et al. |
| 5,612,886 A | 3/1997 | Weng |
| 5,623,109 A | 4/1997 | Uchida et al. |
| 5,663,894 A | 9/1997 | Seth et al. |
| 5,710,723 A | 1/1998 | Hoth et al. |
| 5,745,382 A | 4/1998 | Vilim et al. |
| 5,745,654 A | 4/1998 | Titan |
| 5,754,965 A | 5/1998 | Hagenbuch |
| 5,761,640 A | 6/1998 | Kalyanswamy et al. |
| 5,784,285 A | 7/1998 | Tamaki et al. |
| 5,808,903 A | 9/1998 | Schiltz et al. |
| 5,822,212 A | 10/1998 | Tanaka et al. |
| 5,845,230 A | 12/1998 | Lamberson |
| 5,848,396 A | 12/1998 | Gerace |
| 5,921,099 A | 7/1999 | Lee |
| 5,933,352 A | 8/1999 | Salut |
| 5,940,812 A | 8/1999 | Tengel et al. |
| 5,956,487 A | 9/1999 | Venkatraman et al. |
| 5,987,399 A | 11/1999 | Wegerich et al. |
| 5,991,525 A | 11/1999 | Shah et al. |
| 5,993,041 A | 11/1999 | Toba |
| 5,995,916 A | 11/1999 | Nixon et al. |
| 6,000,832 A | 12/1999 | Franklin et al. |
| 6,009,381 A | 12/1999 | Ono |
| 6,021,396 A | 2/2000 | Ramaswamy et al. |
| 6,026,348 A | 2/2000 | Hala |
| 6,029,149 A | 2/2000 | Dykstra et al. |
| 6,076,088 A | 6/2000 | Paik et al. |
| 6,128,540 A | 10/2000 | Van Der Vegt et al. |
| 6,131,076 A | 10/2000 | Stephan et al. |
| 6,141,647 A | 10/2000 | Meijer et al. |
| 6,141,674 A | 10/2000 | Unkrich et al. |
| 6,144,893 A | 11/2000 | Van Der Vegt et al. |
| 6,181,975 B1 | 1/2001 | Gross et al. |
| 6,202,038 B1 | 3/2001 | Wegerich et al. |
| 6,240,372 B1 | 5/2001 | Gross et al. |
| 6,356,857 B1 | 3/2002 | Qin et al. |
| 6,393,373 B1 | 5/2002 | Duyar et al. |
| 6,424,958 B1 | 7/2002 | Pappalardo et al. |
| 6,502,082 B1 | 12/2002 | Toyama et al. |
| 6,519,552 B1 | 2/2003 | Sampath et al. |
| 6,522,978 B1 | 2/2003 | Chen et al. |
| 6,556,939 B1 | 4/2003 | Wegerich |
| 6,567,752 B2 | 5/2003 | Cusumano et al. |
| 6,567,795 B2 | 5/2003 | Alouani et al. |
| 6,587,737 B2 | 7/2003 | Voser et al. |
| 6,609,036 B1 | 8/2003 | Bickford |

(Continued)

OTHER PUBLICATIONS

Choi et al. Computers and Chemical Engineering 28 (2004) 1377-1387.*

International Search Report of the International Searching Authority, International Application No. PCT/US2011/020094, Mar. 22, 2011, 2 pages.

Povinelli et al. Time series classification using Gaussian mixture models of reconstructed phase spaces. IEEE Transactions on Knowledge and Data Engineering, vol. 16(6): 779-783 (Jun. 2004), p. 780.

Wong, Analysis and augmentation of multi-parameter monitoring system for early warning of patient deterioration. Mar. 12, 2007, p. 19-21.

Tarassenko, L.; Hann, A.; Patterson, A.; Braithwaite, E.; Davidson, K.; Barber, V.; Young, D., "BIOSIGN™: multi-parameter monitoring for early warning of patient deterioration," Medical Applications of Signal Processing, 2005. The 3rd IEE International Seminar on (Ref. No. 2005-1119) , vol., No., pp. 71,76, Nov. 3-4, 2005.

(Continued)

Primary Examiner — Michael Borin

(57) ABSTRACT

Ambulatory or in-hospital monitoring of patients is provided with early warning and prioritization, enabling proactive intervention and amelioration of both costs and risks of health care. Multivariate physiological parameters are estimated by empirical model to remove normal variation. Residuals are tested using a multivariate probability density function to provide a multivariate health index for prioritizing medical effort.

31 Claims, 8 Drawing Sheets

(56) References Cited

U.S. PATENT DOCUMENTS

| | | |
|---|---|---|
| 6,625,569 B2 | 9/2003 | James et al. |
| 6,651,035 B1 | 11/2003 | Lang |
| 6,775,641 B2 | 8/2004 | Wegerich et al. |
| 6,858,431 B2 | 2/2005 | Hair |
| 6,859,739 B2 | 2/2005 | Wegerich et al. |
| 6,876,943 B2 | 4/2005 | Wegerich |
| 6,892,163 B1 | 5/2005 | Herzog et al. |
| 6,898,469 B2 | 5/2005 | Bickford |
| 6,917,839 B2 | 7/2005 | Bickford |
| 6,941,287 B1 | 9/2005 | Vaidyanathan et al. |
| 6,952,662 B2 | 10/2005 | Wegerich et al. |
| 6,957,172 B2 | 10/2005 | Wegerich |
| 6,975,962 B2 | 12/2005 | Wegerich et al. |
| 7,031,857 B2 | 4/2006 | Tarassenko et al. |
| 7,085,675 B2 | 8/2006 | Wegerich |
| 7,089,154 B2 | 8/2006 | Rasmussen et al. |
| 7,142,990 B2 | 11/2006 | Bouse et al. |
| 7,233,886 B2 | 6/2007 | Wegerich et al. |
| 7,308,385 B2 | 12/2007 | Wegerich et al. |
| 7,318,808 B2 | 1/2008 | Tarassenko et al. |
| 7,373,283 B2 | 5/2008 | Herzog et al. |
| 7,403,869 B2 | 7/2008 | Wegerich et al. |
| 7,409,320 B2 | 8/2008 | Wegerich |
| 7,539,597 B2 | 5/2009 | Wegerich et al. |
| 7,640,145 B2 | 12/2009 | Wegerich et al. |
| 7,647,185 B2 | 1/2010 | Tarassenko et al. |
| 7,670,295 B2 | 3/2010 | Sackner et al. |
| 7,739,096 B2 | 6/2010 | Wegerich et al. |
| 7,818,131 B2 | 10/2010 | Mott |
| 7,941,209 B2 | 5/2011 | Hughes et al. |
| 7,941,701 B2 | 5/2011 | Wegerich et al. |
| 8,239,170 B2 | 8/2012 | Wegerich |
| 8,290,575 B2 | 10/2012 | Tarassenko et al. |
| 8,332,017 B2 | 12/2012 | Tarassenko et al. |
| 2003/0055666 A1 | 3/2003 | Roddy |
| 2003/0126258 A1 | 7/2003 | Conkright |
| 2005/0261837 A1 | 11/2005 | Wegerich |
| 2006/0293859 A1* | 12/2006 | Pipke et al. .................... 702/19 |
| 2007/0149862 A1 | 6/2007 | Pipke |
| 2008/0071501 A1 | 3/2008 | Herzog |
| 2009/0177443 A1 | 7/2009 | Nikovski et al. |
| 2011/0029250 A1* | 2/2011 | Mott ............................... 702/19 |
| 2011/0087115 A1 | 4/2011 | Sackner et al. |
| 2011/0093244 A1* | 4/2011 | Pipke et al. .................... 703/2 |
| 2011/0124982 A1* | 5/2011 | Pipke ............................ 600/301 |
| 2011/0257555 A1 | 10/2011 | Banet et al. |
| 2012/0029320 A1 | 2/2012 | Watson et al. |

OTHER PUBLICATIONS

Nairac, A.; Corbett-Clark, T.A.; Ripley, R.; Townsend, N.W.; Tarassenko, L., "Choosing an appropriate model for novelty detection," Artificial Neural Networks, Fifth International Conference on (Conf. Publ. No. 440), vol., No., pp. 117,122, Jul. 7-9, 1997.

Tarassenko L, Hann A, Young D. "Integrated monitoring and analysis for early warning of patient deterioration," Br J Anaesth. Jul. 2006;97(1):64-8. Epub May 17, 2006.

* cited by examiner

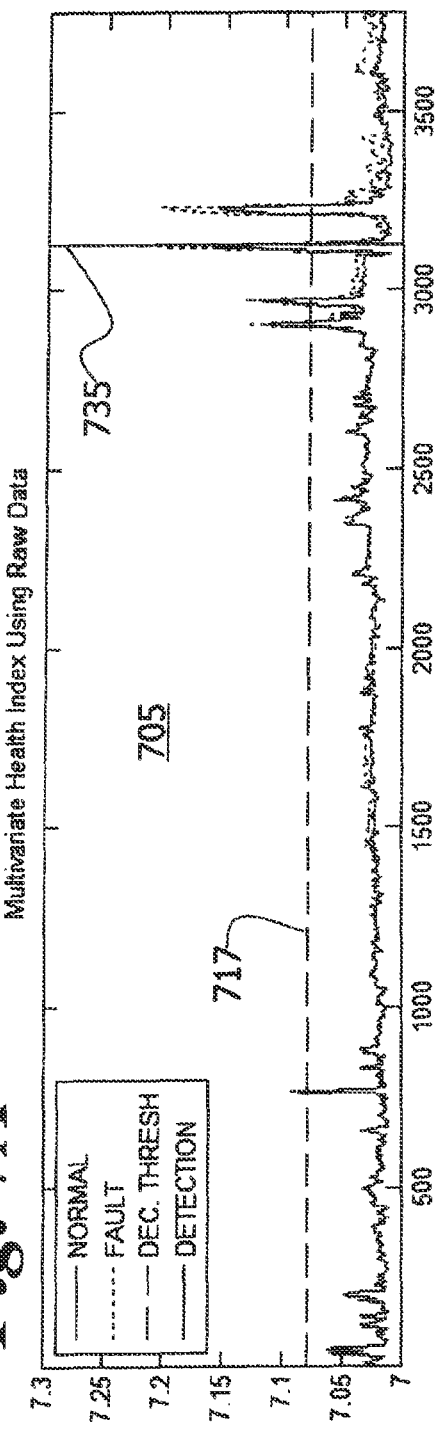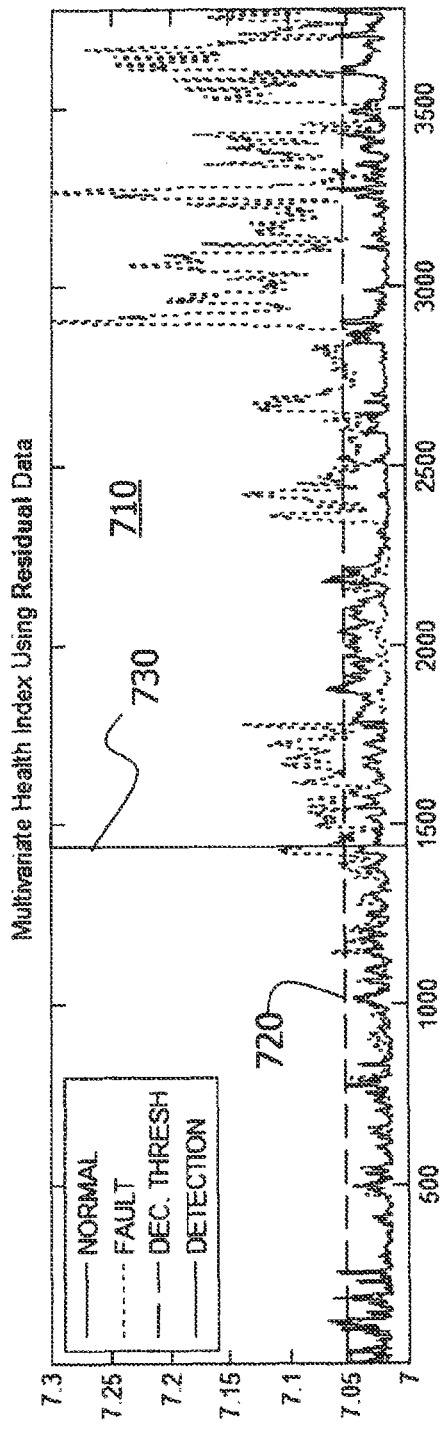
Fig. 7A
Fig. 7B

MULTIVARIATE RESIDUAL-BASED HEALTH INDEX FOR HUMAN HEALTH MONITORING

CROSS REFERENCE TO RELATED APPLICATIONS

This application claims the benefit of priority under 35 U.S.C. §119(e) to U.S. Provisional Patent Application Ser. No. 61/295,072 filed Jan. 14, 2010, which is fully incorporated herein for all purposes.

STATEMENT REGARDING FEDERALLY SPONSORED RESEARCH OR DEVELOPMENT

This invention was made with Government support under award number IIP-0810751 awarded by the National Science Foundation. The Government has certain rights in this invention.

BACKGROUND OF INVENTION

1. Field of the Invention

The present invention relates generally to the field of human health monitoring, and more particularly to the use of multivariate models for analysis of measurements of biological parameters to provide residual-based assessment of human health indicators.

2. Brief Description of the Related Art

Medicine has for centuries been practiced as a reactive, crisis-driven process. Unfortunately, it remains largely so to this day. Chronic diseases represent a disproportionate share of the crushing economic cost of healthcare, much of which could be avoided by early warning of deterioration. Current healthcare practices are episodic and reactionary, with little visibility into patient health outside the controlled setting of the clinic or hospital. However the medical arts are only now beginning to explore out-patient telemetry from wearable devices, and there is virtually no answer to who is going to watch all this data, or how it will be analyzed to provide early warning with a low false alert rate. Moreover, out-patient telemetry poses considerable challenges due to ambulatory motion artifact and normal physiology variation in the course of daily activities not usually dealt with when a patient is sedated and supine in a hospital bed.

Other industries (nuclear, aviation, refining, computer systems) have in recent years adopted advanced intelligent algorithms for condition monitoring, that accommodate normal variation and dynamics exhibited in the sensor data collected from a target system, and differentiate it from subtle early warning signs of deterioration. One kind of machine learning technique, Similarity-Based Modeling ("SBM") technology, has proven successful in many applications including those mentioned above. SBM is a nonparametric data driven modeling technique which learns normal behavior from multivariate data from a complex system, and distinguishes it from the onset of adverse behavior in a monitored system.

Visibility into health issues with SBM is contingent on the availability of multivariate data. Continuous telemetry from a wearable sensing device with multiple sensors could provide such data. However, existing devices are data-poor, in most instances univariate, and are primarily aimed at very narrow health related issue, e.g. glucose monitoring for diabetics, or blood pressure for hypertension. The devices are usually not meant for continuous monitoring, and any analysis performed is done using gross population statistics, i.e. not personalized to the individual. Further, current commercial telehealth devices are not easily wearable, and do not take advantage of the latest mobile technologies.

There is a need to make multivariate continuous data available for analysis, whether from a wearable device on an out-patient basis or from bedside equipment in a hospital, so that machine learning technology like the aforementioned SBM can be applied to automate early detection of incipient changes indicating the health of the patient is potentially subject to deterioration. Because medical staff is commonly overworked and short on time to spend deeply studying analytical results for each patient, especially where large populations of at-home patients may be involved, an important issue is how to summarize the results of such machine learning techniques in a simple metric for actionability.

SUMMARY OF THE INVENTION

An end-to-end human health monitoring solution is disclosed, comprised of a wearable wireless sensing device that continuously collects vital signs sensor data and transmits it (in real-time or in periodic bursts) to a base-station computer (or cell-phone/PDA) for preprocessing. The preprocessed data is then sent to a server over the web for analysis using a kernel-based machine learning analytical method tailored for human monitoring, such as SBM. The SBM technology is trained to be specific to each individual's normal vital signs characteristics. Due to the variation in vital signs data from human to human, this capability is crucial for any human monitoring system to be effective.

The server can be remotely located from the patient. The analysis performed at the server with SBM or other related kernel-based method works by generating estimates of the vital signs (i.e., physiological data) that have been determined from the sensor data. These estimates represent what a trained SBM model can determine as the closest allowable normal physiological data that corresponds to the monitored data. The estimates made of the physiological data are differenced with the actual, monitored physiological data to generate residuals, representing the differences between the expected values according to the trained model, and what has been measured by the wearable sensing device. These residuals form the basis for further analysis that provides early detection of subtle warning of health problems, which would likely be missed using conventional medical methods of comparing vital signs to demographically acceptable ranges (e.g., population-based standards for blood pressure).

Residuals for normal physiology (physiology as previously modeled) are different from residuals for physiology that is beginning to deviate from normal, and can be statistically distinguished. The further computerized analysis of the residuals comprises one or more of the steps of: determining a likelihood that the residuals derived for any given multivariate input observation of monitored data are representative of a pattern of residuals characteristic of normal physiology, based on a "mixture of Gaussians" density estimation; generating a multivariate health index based on that likelihood as a logarithm of the inverse of the likelihood; applying a threshold to the index thus generated to render a decision whether the inputted vital signs are characteristic of normal physiological behavior; and combining a series of such decisions to provide an early indication of deviation from normal of the physiological health of a patient. The multivariate health index advantageously summarizes the residual analysis from multiple variables into a single index for the management of prioritized lists of patients.

The health monitoring solution can also be applied to multivariate physiological parameters obtained in a hospital from bedside monitors. An SBM model of typical human physiology can be used to make estimates and residuals for patients in the hospital, particularly those at risk for developing complications such as sepsis or pneumonia, and particularly patients who are sedated and/or ventilated and not able to express discomfort or feelings of incipient illness. Bedside data feeds amenable to the health monitoring solution include electrocardiographs, pulse oximeters, ventilator data, arterial and venous pressures measured by noninvasive means or by catheters, and the like. Such data can be streamed to a server for the hospital ward, or to offsite servers for monitoring multiple hospital facilities, and decision support can be rendered by application of SBM to these data streams and displayed to healthcare workers for prioritizing patient treatment.

The analytics of the present invention can be performed on generic computing platforms specially configured by software. Data collected from sensors on the patient can be wirelessly transmitted to an ambulatory or portable device, e.g., via Bluetooth or other extremely local radio protocol. The portable device can be a cell phone carried by the patient, a "personal digital assistant", PDA, or the like, or a portable computing device moved with a patient in the hospital bed. This device may receive raw sensor signals and perform the aforementioned preprocessing to extract vital sign "features" (physiological data) from the sensor signals, for example a heart rate from an EKG/ECG signal; or may receive already-preprocessed features extracted by sensor microprocessing facilities from raw sensor signals. The resulting physiological "feature" data can be analyzed with SBM either on the device (the cell phone or PDA) or on a computer/server to which such physiological data is transferred. The computer can be a home computer collocated with the patient, or can be a remote server at an analytics data center. The transfer of data from the device can be by means of cabled offload or by wireless retransmission.

BRIEF DESCRIPTION OF THE DRAWINGS

The novel features believed characteristic of the invention are set forth in the appended claims. The invention itself, however, as well as the preferred mode of use, further objectives and advantages thereof, is best understood by reference to the following detailed description of the embodiments in conjunction with the accompanying drawings, wherein:

FIG. 5 is a multi-chart example plot showing in the top four plots raw physiologically-related signals, and in the bottom five plots the related feature data derived there from;

FIG. 7A is one of a pair of related plots of a multivariate health index and has been derived merely for raw feature data showing an index for unperturbed data and for perturbed data;

FIG. 7B is a multivariate health index plot derived for residual data generated from kernel-based models of feature data showing and index for unperturbed data and for perturbed data.

DETAILED DESCRIPTION OF THE PREFERRED EMBODIMENTS

Figure 1:
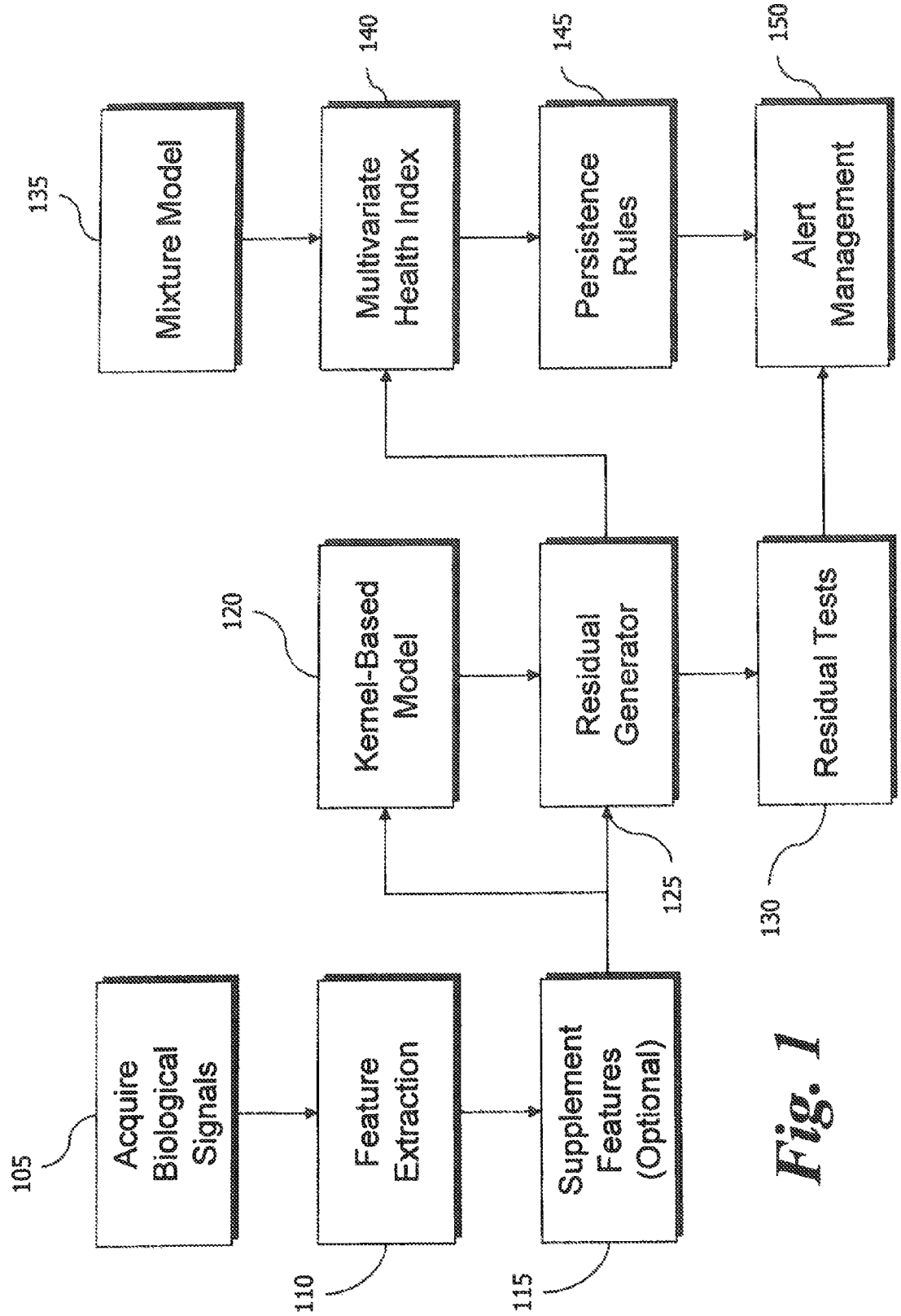
FIG. 1 is a block diagram showing a general arrangement according to one embodiment.

There are a plethora of chronic ailments and illnesses of which a patient may suffer, but for which the patient cannot be kept indefinitely in a hospital. A patient may have heart failure, chronic obstructive pulmonary disease, renal failure, diabetes, early stage dementia and other conditions, which can devolve from a stable, managed state into an emergency health risk with little apparent warning. It is desirable to detect such devolution early because medical intervention at the early stage can prevent the emergency, avoid costs, prevent disease progression, and improve outcomes.

Even patients in the hospital under care of medical staff can develop complications that are best detected early. Patients on ventilators suffer a high rate of developing pneumonia. Infection and sepsis can occur due to hospital-acquired cross-contaminant infections or from post-surgical complications. Conventional bedside monitoring typically employs thresholds on vital signs to alert staff of patient deterioration, but these conventional alerting methods are coarse, either suffering a high false alert issue and rapidly disappearing into the ignored background noise, or catching the deterioration later than is desired.

Unlike the majority of monitoring approaches used in the healthcare industry today, SBM is a multivariate approach that takes advantage of the interrelationships between vital signs signals (e.g., heart rate (HR), blood oxygen saturation (SpO2), Respiration Rate, Blood Pressure). Such an approach is critical for the analysis of physiology in the presence of normal variation, that is, variation of physiological data due to normal changes in physiology responsive to metabolic needs, activity, environment, diurnal cycles and the like. Over the course of a day, a typical human exhibits a wide range of heart rates, respiration rates, blood pressures, blood oxygen levels and so on. In contrast to a sedated patient in a hospital setting, ambulatory conditions are exceptionally plagued by such variation, and as a result there has been little traditional medical monitoring of humans in their normal lives at home except in extremely controlled circumstances. Even in a sedated condition in the hospital, normal patient physiology still exhibits substantial variation. Such variation hides early changes in physiological parameters that evidence incipient deterioration of health. Conventional alerts placed on single parameters cannot see such changes against the background of normal variation until such changes become extreme. For example, a threshold placed on heart rate cannot be set to trigger an alert merely because the heart rate rises by 10 beats per minute, because this may readily occur in normal physiology. But if the threshold is set to 160 bpm, a patient's condition may already have deteriorated substantially by the time the threshold is exceeded.

In addition, much of the sensing technology being developed today is burdened by the necessity to provide an exactly calibrated reading of the vital sign of interest. In contrast, SBM requires only relative proxies of the vital sign of interest, thereby avoiding the problem of attaining absolute calibration of a physiological parameter in order to measure health. This is because the detection of incipient health problems is based on relative changes between all biosignals in aggregate, not on exceedances from population-based vital sign ranges.

SBM achieves these advantages by embodying normal variation in a model ("learning"). This model is then used to generate multivariate estimates of the learned physiological parameters when presented with a multivariate measurement of those parameters. These estimates represent the closest possible set of values for normally varying physiology, to the presented (measured) values. The estimates are differenced with the presented values to yield residuals. Analysis is advantageously shifted from testing raw physiological values which are plagued by normal variation, to testing residuals which represent differences beyond merely normal variation. In effect, SBM removes normal variation by subtracting the estimated behavior from the measured behavior, leaving just deviations.

As described herein, the residuals are analyzed using a multivariate density estimation technique. According to this novel approach, the multidimensional distribution of residual vectors (vectors of dimension n where n is the number of physiological parameters for which estimates were differenced with actual measured values) for data representative of the patient's normal physiology is used to form a multivariate density estimator. The density estimator is a Gaussian mixture model, and is used to determine the likelihood that any new input residual vector (i.e., from newly monitored data) is part of the same distribution. This likelihood obtained from the multidimensional density estimator effectively consolidates the behaviors of the individual residuals for each of the physiological parameters, into one overall index that can be used to summarize patient priority. This likelihood can be used as a multivariate health index (MHI), and can be subsequently tested with a number of persistence rules to assess patient priority over a time series of observations of the multiple physiological parameters being monitored.

Advantageously, this MHI analysis of model-generated residuals provides earlier warning of incipient health issues when compared to conventional medical univariate thresholds on raw physiological data, and when compared to multivariate density estimates of raw physiological data.

Turning to FIG. 1, the overall approach can be appreciated. In step 105, multiple biosignals are acquired from sensors on or in the patient. Examples of appropriate biosignals include electrocardiographs (ECG), thoracic bioimpedance (bio-Z), photoplethysmographs (PPG), temperature differentials, systolic or diastolic blood pressures, accelerometer-measured motion, piezoelectric signals of respiratory activity, and instant airflow measurements from respiration, to name a few. In step 110, these biosignals are used to derive physiological feature data. A variety of physiological features can be derived from such biosignals, with a commonly understood example being heart rate determined from landmarks of the ECG signal. Similarly, thoracic bioimpedance can yield respiratory rate and depth; PPG can yield pulse transit time (when cross referenced to the ECG) and the blood oxygen saturation, and so on. A variety of physiological features are known in the art, and the application of SBM in subsequent steps readily contemplates the use of new features as well, because the method is agnostic to the signals used (as long as the model is trained on the same kind of data) so long as they interrelate through the feedback loops and control mechanisms of human physiology. In optional step 115, the derived features can be supplemented with other physiologically-relevant data, that is, data that impacts the physiological behavior or response of the monitored human. An example is FiO2, the fraction of oxygen in inspired air, which can be increased over room air with the use of supplementing oxygen. In step 120, a kernel-based model such as SBM that has been trained on normal variation of these same physiological features generates estimates of an input observation of the features. Typically, an estimate is made for all elements in an input vector comprised of the collection of physiological parameters sampled contemporaneously. In step 125, the residuals are generated between those features measured and corresponding estimates of those features, in the instant monitored observation. Optionally, threshold tests can be applied in a univariate manner or in a multivariate pattern-matching manner to the residuals in step 130. In parallel with that option, the residuals are processed in step 135 by a mixture model developed from "normal" residuals, and a multivariate health index is determined for the input observation in step 140. This MHI is an index of the likelihood that the residuals from the input observation belong to the multivariate distribution of the mixture model. The MHI can also be tested with a threshold to determine if the likelihood is insufficient such that the input observation evidences deviations not characteristic of normal physiology. In step 145, persistence rules can be applied to a time series of MHI determinations to further test observation-over-observation in time the persistence of threshold exceedances, providing greater confidence that a deviation is occurring in the patient's health, and is not merely a transient phenomenon in the data. In a step 150, the alerts from the MHI and its test, along with any previous tests on individual residuals or residual patterns, is managed for prioritization of patient care via a user interface. Alert management can facilitate user-initiated annotations into a medical record system relating to the alerts of "dismissal", "elevation" or "monitor" and other actions.

The biosignals of step 105 can be acquired from typical hospital vital signs equipment such as bedside monitors and ventilators, from mobile vital signs monitors, implanted devices such as implantable cardioverter defibrillators and pacemakers with instrumentation, and from wearable ambulatory monitors. Whatever data source device is used, it must collect biosignals capable of providing multiple related physiological variables or features contemporaneously and at least periodically, if not continuously. In one form, a patient uses a non-invasive ambulatory sensing device or has an implantable device to acquire biosignals on at least a semi-continuously basis throughout the patient's normal daily activities. Data acquired by a sensing device can be offloaded from device memory on a periodic basis and thereafter processed on a computer; or can be continuously transmitted by cellular network or WiFi, to be processed either continuously or in batch-mode by a receiving computer or server. The physiological features can even be analyzed using the residual-based method on a smartphone or PDA, carried by the patient, since the computing requirements of the analytical process are well within the capabilities of modern mobile devices. Then, resulting alerts or health status conditions can be reported locally on the mobile device, and can also be uploaded to a central server to be shared with medical practitioners.

One non-invasive wearable sensing device that can be used with the present invention is designed to acquire data from 4 types of signals: ECG, red and infrared (IR) photoplethysmograph (PPG), bioimpedance, and a 3-axis accelerometer. These sensors provide a rich waveform set from which physiologic features can be extracted. The extracted features (as opposed to the raw waveform data) are what ultimately drive the SBM-based human health monitoring approach. The device can be designed to record relevant biosignals for local storage, e.g., on an onboard microSD card; or for transmission via a built-in Bluetooth radio to a cell phone or PDA carried by the patient. The device can be designed to have a USB Mini-B connector that can be used to supply power to the device when recharging its battery, and that provides a mechanism for high-speed communication with a PC for periodically off-loading data, if raw real-time sensor data are stored on a micro-SD card of the device. The device may use a microprocessor selected from the well known Texas Instruments MSP430 line, ideal given its low power consumption characteristics, built-in ADC, DAC, timers, and multiple serial peripheral interfaces (SPI/UART/I2C). The Bluetooth interface can be provided via a BlueCore 3 Plug-n-Go IC, a 96-pin BGA module from CSR, Inc., with minimal external component requirements, and a 2.4 GHz chip antenna.

A number of sensing interfaces can be used to provide data for the present invention. The electrocardiogram (ECG) can be implemented by using a two-stage analog high pass filter (HPF), followed by a radio-frequency interference (RFI) filter and a micro-power instrumentation amp. It is crucial in an ambulatory mode to employ an RFI filter in front of this high gain differential amplifier. Without it, a phenomenon called RF rectification can occur in the differential amplifier IC. Once an RF signal becomes rectified inside the IC, it results in a DC offset error at the output and no amount of low pass filtering can remove the error. As the RFI changes over time the DC offset changes as well resulting in an ECG signal that is highly susceptible to artifacts. Two pickup electrodes can be used to acquire the signal, for example on either side of the chest. The ECG is typically sampled at 12 bits and 256 Hz by the microprocessor.

A bioimpedance measurement can be made by using a dedicated 12-bit impedance converter network analyzer IC (Analog Devices AD5933) in conjunction with a voltage to current stage and a programmable gain instrumentation amplifier. An electrode placed under the left armpit can be used to inject 425 µA of current at 50 kHz to a ground electrode found on the opposite side of the torso. The same electrodes used to pickup the ECG signal can be used to pick up the 50 KHz signal through a 5 KHz HPF and an RFI filter. The difference in voltage is proportional to body's impedance through the relationship V=IR. The AD5933 IC is capable of measuring the complex impedance of the signal.

The PPG signal can be acquired by controlling a pair of LEDs (Red and Infrared) via a current limiting H-Bridge for light generation. The unabsorbed light is measured using a reverse-biased PID photodetector connected to a transimpedance amplifier for initial gain. The measured signal is then fed to a second stage differential amplifier along with a DC-offset value generated in firmware from the output of the microprocessor's DAC. The DC-offset value is meant to keep the signal within the rails of the differential amplifier so that the signal gain can be maximized. The output of the second stage amplifier is preferably then oversampled by a factor of 8 at 16384 Hz (for a final sampling rate of 256 Hz) after a waiting period of 488 µS after the LEDs have changed states. The oversampling is applied to increase the signal-to-noise ratios of the PPG signals, which are highly susceptible to noise.

Accelerometer data can be generated by a LIS302DL MEMS digital accelerometer at 400 Hz (8 bits per axis). The digital readings are preferably read by the microprocessor at a rate of 100 Hz.

The acquired data can be placed into two buffers: one that is flushed out to the file system (micro-SD), and one that is fed to the Bluetooth IC for transmission. Each value is preceded with a single byte ID for identification, and periodic "sync" blocks are inserted into the Bluetooth stream to aid in data alignment. Each packet of data consists of the ID byte, followed by two bytes containing the sample value. Periodic 32-bit timestamps are also transmitted by utilizing two packets to represent the high and low words of a 32-bit seconds counter.

Figure 2:
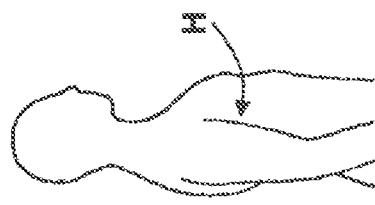
FIG. 2 shows an example of sensor placement on a human.
Figure 2:
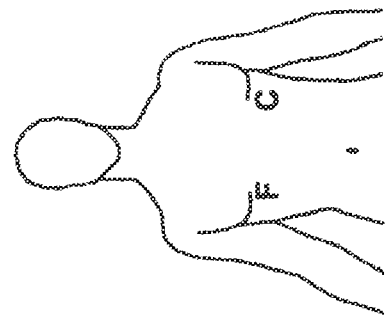
Figure 2:
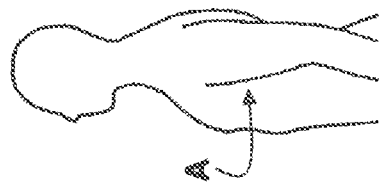
Figure 3:
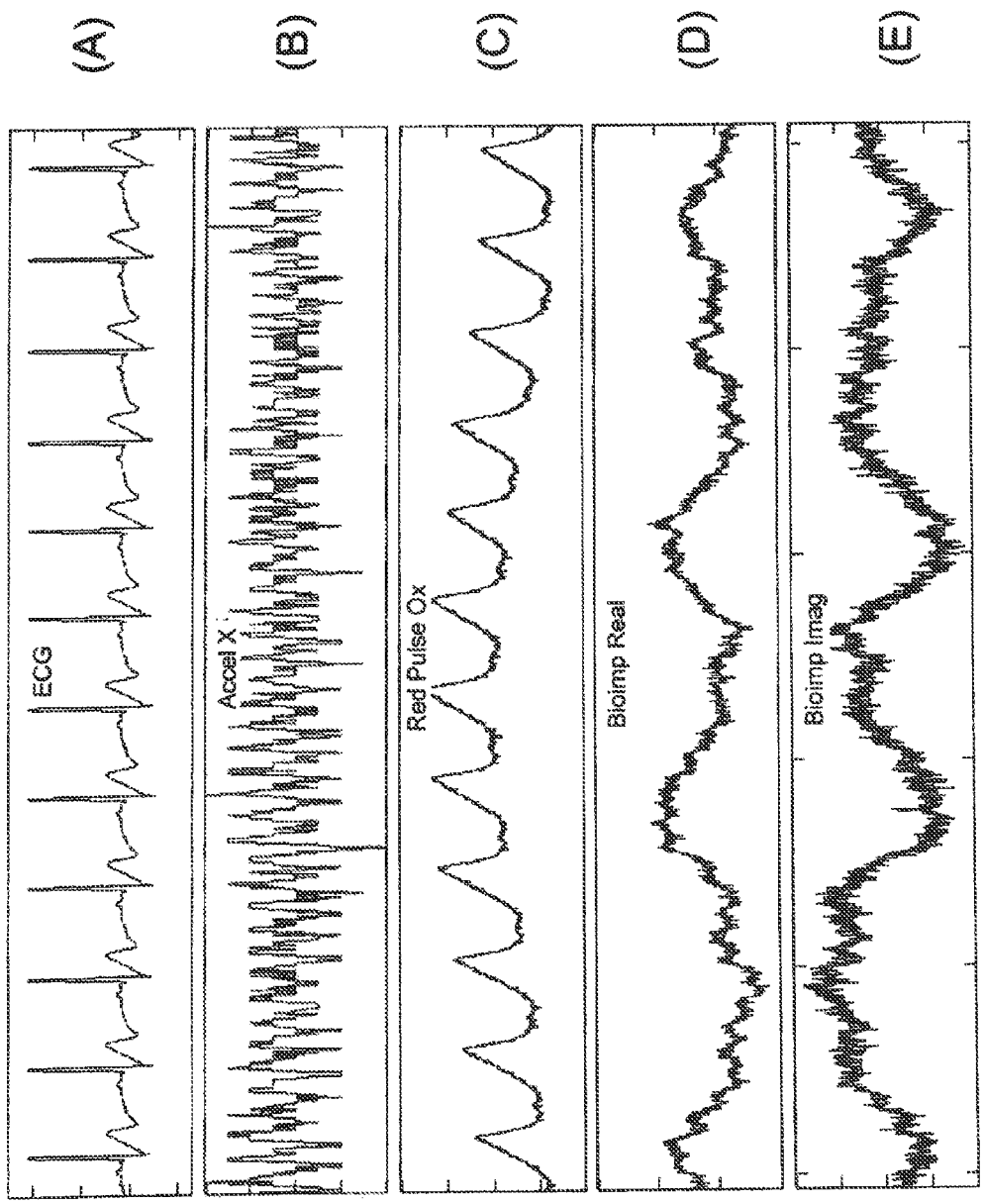
FIG. 3 shows an example chart of raw physiological waveforms or signals.

In one form, a subject is outfitted with four electrodes and one pulse oximetry sensor. Two types of electrodes can be used, carbon-rubber non-adhesive electrodes and carbon-rubber adhesive electrodes, although other commercially available electrodes are readily contemplated for use in the embodiment. The electrodes are placed on the body as shown in FIG. 2: (A) corresponds to the Bioimpedance current source electrode, (C) is the +ECG electrode, (F) is the -ECG electrode, and (H) is the analog ground electrode (AGND). The ECG leads are also used to simultaneously pick up the bioimpedance response signal. The device can be worn by either being placed in a stretchable chest strap with the non-adhesive electrodes attached to the inside of the strap via Velcro, or it is placed in a pouch worn around the neck with leads running to the adhesive electrodes. The PPG signal is acquired via a disposable Nelicor reflective pulse oximetry sensor affixed to the forehead and connected to the device. A typical example of the signals captured by the wearable sensing device described above from a human subject is shown in FIG. 3. The signals are: (A) ECG, (B) x-axis accelerometer, (C) infrared photoplethysmograph (PPG), (D) real component of bioimpedance, and (E) imaginary component of bioimpedance. Not shown are the y and z axis accelerometer signals, and the red PPG signal which are all captured as well.

Turning now to physiological feature generation, the raw data collected from the wearable device is not directly analyzed with SBM. Instead a set of physiological features are derived from the raw waveform data. These derived features are what provide the insight into the status of human cardiopulmonary control system and in turn the overall health of an individual. According to one example, several features from two categories can be used, cardiac derived and respiratory derived. The cardiac derived features are heart rate (HR), pulse transit time (PTT) and the Red absorption to IR absorption PPG ratio (or Q). In one example, the HR feature can be obtained directly by measuring the interval between consecutive QRS peaks in the ECG signal. The peaks are detected using a multi-step procedure. First a digital HPF is applied to the ECG signal. Then the filtered signal is split into 10 second data windows that are de-trended to remove a straight line fit to the data. Next, within each window, the 98th percentile is calculated and the locations of all samples above the 98th percentile are found. All samples found reside on a set of local peaks within the 10 second window. The last step is to find the sample location of the maximum value for each of the local peaks within the window. These locations are the individual QRS peaks in the ECG waveform. Then the HR rate is simply the reciprocal of the time interval between each heart beat.

PTT is the delay time between the QRS peak and PPG pulse peak. This feature is known to be inversely proportional to blood pressure. To calculate it, the robustness of the ECG QRS peak detection algorithm is exploited with first principles. Since it is known that a transit time of more than 250 ms is unlikely in a human, 250 ms windows starting from the QRS peak location for each heart beat can be used to search for the corresponding PPG peak. The maximum value within the window is the PPG peak. This is done for both the red and IR PPG signals. Because the PPG signals tend to be naturally noisy, before the peaks are located, the PPG signals are first digitally filtered using a median filter (to remove spiking) followed by a band-pass filter with lower and upper cutoff frequencies of 0.5 Hz and 5 Hz respectively.

Figure 4:
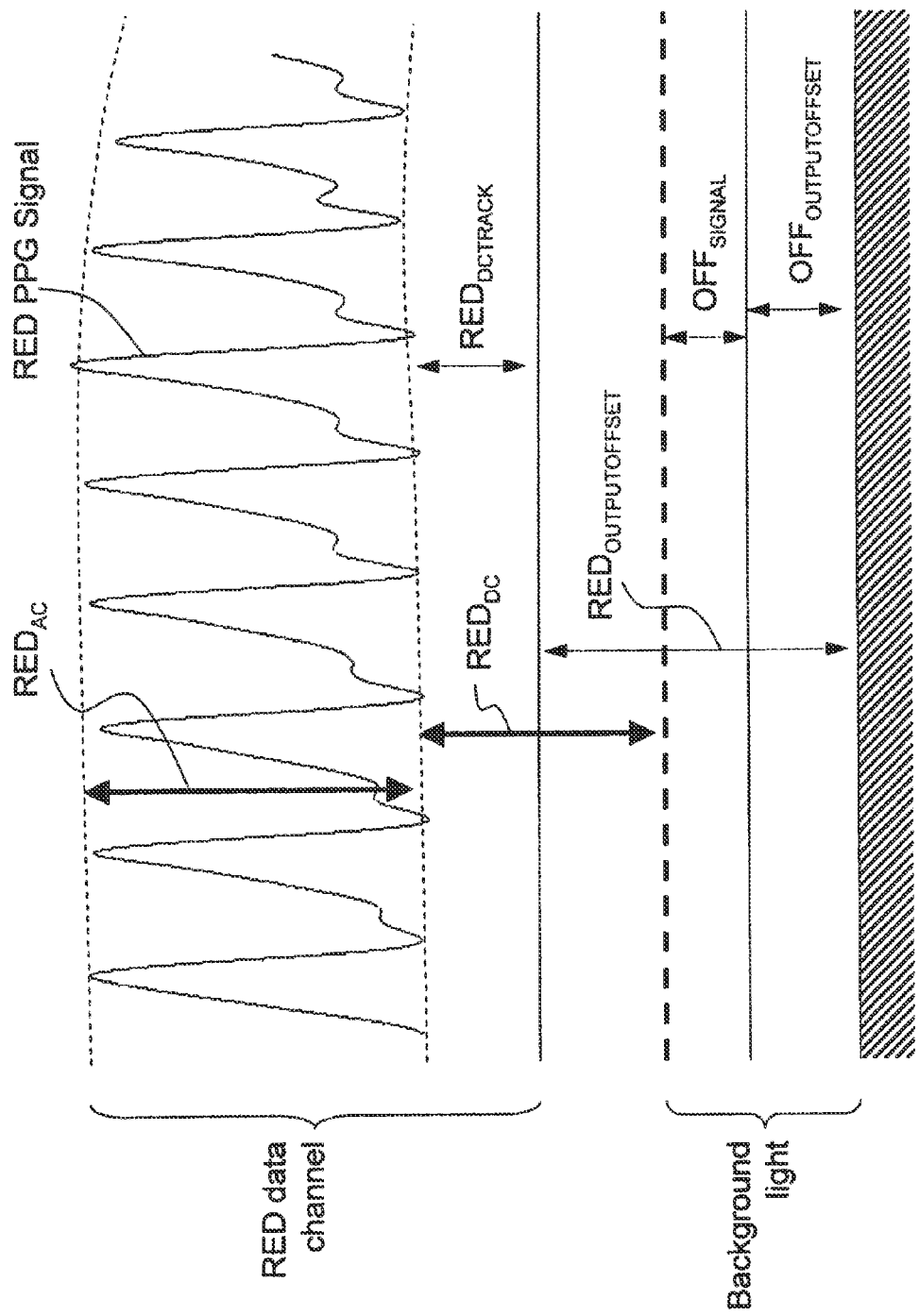
FIG. 4 shows a signal amplitude chart of photoplethysmography components used to determine a feature related to SpO2 (blood oxygen saturation), which may be understood to represent the light components picked up by a photosensor stacked additively.

The Q feature is the ratio of the blood absorption of red light to infrared light. Q is inversely known to be proportional to SpO2 (blood oxygen saturation). Calculating Q is more complicated due to the analog and digital signal processing that takes place before the raw PPG data are acquired. With reference to FIG. 4, Q is calculated as follows. The basic equation for Q is given by $$Q = \frac{(RED_{AC}/RED_{DC})}{(IR_{AC}/IR_{DC})} \quad (1)$$

Here $RED_{AC}$ ($IR_{AC}$) is the amount of red (infrared) light absorbed by the blood and REDDC ($IR_{DC}$) is the amount of red (infrared) light absorbed by the surrounding tissue. The PPG implementation comprises an LED driving stage, a PID photodiode with a transimpedance amplifier, and a second gain stage which subtracts out a DC offset (RED OUTPUTOFFSET in the FIG. 4) and adds additional gain. Some level of background light is detected by the sensor, and needs to be subtracted from the measured signal as well (OFF SIGNAL+ OFF OUPUTOFFSET). The RED DC TRACK parameter is the lower envelop of the actual acquired signal. Then Q can be given by the following equations (shown for red only).

$$RED_{AC} = \alpha RED'_{AC} \quad (2)$$

$$RED_{AC} = \alpha(RED_{DCTRACK}) + \beta(RED_{OUTPUTOFFSET}) - \beta(OFF_{OUTPUTOFFSET}) - \alpha(OFF_{SIGNAL}) \quad (3)$$

Here $RED'_{AC}$ is the peak-to-peak value of the actual acquired PPG signal, and $\alpha$ and $\beta$ are scaling factors that are function of the analog to digital converters.

There are two respiratory derived features that can be used in the embodiment, respiration rate (RR) and tidal volume (TV) (or depth of breath). Both are calculated from the bioimpedance signal. The device acquires the real and imaginary parts of the bioimpedance separately. These are combined to form the magnitude which is used for extracting RR and TV. Bioimpedance is highly susceptible to motion artifacts. Muscle movement and organ movement change the impedance of the human body causing undesired variation in the acquired signal. At the same time the signal is noisy and somewhat aperiodic in nature with respect to breathing. Because of these factors one method to obtain reasonable results for extracting RR and TV is a spectral-based approach. The bioimpedance signal is first bandpass filtered with a narrow band digital filter with lower and upper cutoff frequencies of 0.133 Hz and 1 Hz (corresponding to a RR range of 8 to 60 breaths per minute). Next, a sliding window Discrete Fourier Transform (DFT) is applied to the filtered data with overlap to produce feature values every 20 seconds. The RR rate feature corresponds to the frequency at which the maximum value of the magnitude of the DFT occurs in each window. To reduce edge effects each window of data is multiplied with a window function that suppresses the end points to zero before the DFT is calculated. TV is defined to be the value of the magnitude of the DFT at the RR frequency, and quantitatively relates to true tidal volume but is not a directly calibrated measure of tidal volume.

Figure 5:
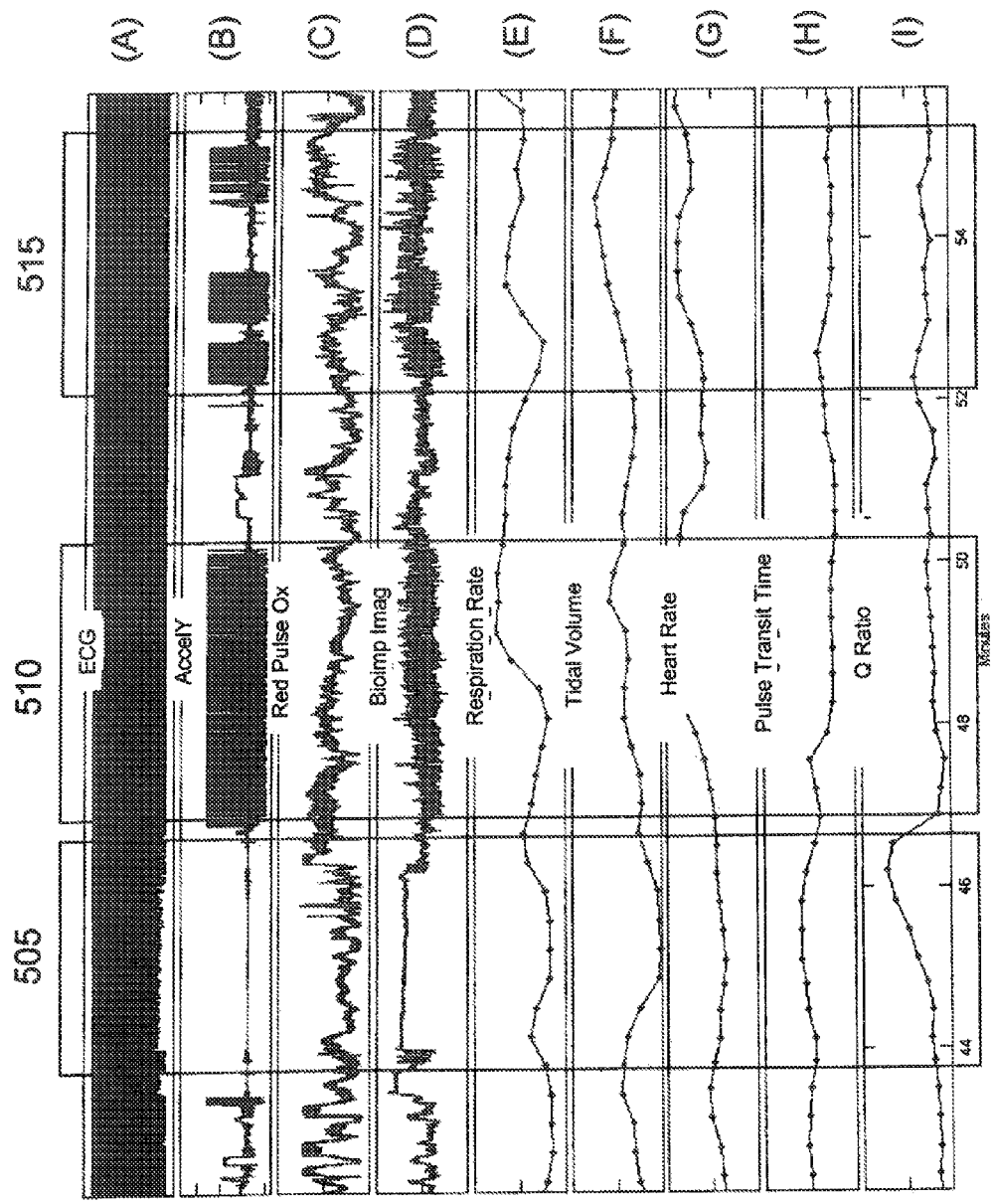

In one form, two last steps are taken to finalize the feature generation process. First, in a noise filtering step that removes spikes and smoothes the feature data at the same time, a moving window trimmed mean filter is applied with 50% window overlap. The default window size is 40 seconds and with an overlap of 50% the resulting filtered features occur at a rate of 1 sample every 20 seconds. The second step is to align all the feature data in time so that they can be analyzed with SBM. This is achieved by interpolating all of the filtered features at the same time points using a shape-preserving piecewise cubic interpolator. An example of the filtered features is shown in FIG. 5 along with some of the raw signals: (A) ECG, (B) y-axis accelerometer, (C) red PPG, (D) bioimpedance magnitude, (E) respiration rate, (F) tidal volume, (G) heart rate, (H) pulse transit time, and (I) red to infrared ratio. Data region 505 occurred while the subject held his breath as is evident by tidal volume (F) going to zero. During the same period the red to IR PPG ratio (I) starts to increase indicating that O2 saturation is lowering. Region 510 occurred while the subject was walking briskly around. After about 45 seconds into the walk his respiration rate, tidal volume and heart rate increase ((E), (F) and (G) respectfully). Pulse transit time drops (H), indicating an increase in blood pressure, while the PPG ratio (I) begins to slowly climb again, indicating lower O2 saturation. Finally region 515 represents the subject running up and down a staircase three times with short rests in between. As expected, similar behavior to that of region 510 is seen.

Invariably sensor noise, artifacts due to sensor movement and other unexpected interference contaminate random time periods of the acquired sensor data. Including tainted data in an SBM model can potentially degrade model performance. SBM is purely data driven and learns normality from the training data. If the training data is contaminated with non-health related artifacts the model's representation of normal will be undesirably broadened. This generally affects its sensitivity in predicting the onset of anomalous behavior.

To deal with sensor noise a number of digital filtering techniques can be applied to either the raw data or to the calculated features themselves. These include the techniques of median filtering, Infinite Impulse Response (IIR) filters and Finite Impulse Response (FIR) filters).

According to one approach, a strategy for detecting artifacts in the raw sensor data is based on a number of components. First, the first order difference of each axis of the accelerometer data is monitored for times when the absolute value of the difference is above a predefined threshold. These times indicate when sudden movements have occurred. Generally, these sudden movements result in transient behavior in the sensor data, most notably in the PPG data and bioimpedance data. The data from all sensors are then ignored from the first indication of sudden movement until 10 seconds after the difference signals falls below the threshold again. This approach works well for detecting transients but does not detect sensor problems. The second component combines heuristic rules with first principles rules to detect sensor and/or feature generation errors. The set of rules is summarized below:

1. If TV<$T_{tv}$ (a threshold constant) then RR is unreliable and is not used. Calculating RR is based on extracting the maximum spectral component of the bioimpedance signal within a narrow band and if TV is below $T_{tv}$ the person is not breathing, or is breathing so shallowly that the maximum component is meaningless; it's just the maximum noise component in the frequency band during this state.
2. If HR>200 or Q (PPG Red to IR ratio)>$T_Q$ (a threshold constant), ignore the calculated feature value. A value of HR above 200 is well above the normal HR for a human so anything above 200 is likely an error. Similarly, Q, a proxy for SpO2, is only realistic in a certain range; however unlike HR the range varies from person to person due to sensor placement and the physical characteristics of the skin. So a unique $T_Q$ is preferably calculated for each individual.

3. If the PTT variance is greater than the HR variance by more than threshold constant $T_{var}$, then ignore the feature data. This means that the pulsatile peaks of the PPG signals are not being identified correctly indicating that the PPG sensor is physically out of place or is being overcome by noise.

Turning now to the process for estimating observations in order to be able to obtain residuals, a number of different kernel-based multivariate estimator methods may be used. What is generally intended by the term "kernel-based" is a multivariate estimator that operates with a library of exemplary observations (the learned data) on an input observation using a kernel function for comparisons. The kernel function generally yields a scalar value (a "similarity") on a comparison of the input observation to an exemplary observation from the library. The scalar similarity can then be used in generating an estimate as a weighted sum of at least some of the exemplars. For example, using Nadaraya-Watson kernel regression, the kernel function is used to generate estimates according to:

$$y_{est} = \frac{\sum_{i=1}^{L} y_i^{out} K(x_{new}, x_i^{in})}{\sum_{i=1}^{L} K(x_{new}, x_i^{in})} \text{ (Inferential form)} \quad (4)$$

$$x_{est} = \frac{\sum_{i=1}^{L} x_i K(x_{new}, x_i)}{\sum_{i=1}^{L} K(x_{new}, x_i)} \text{ (Autoassociative form)} \quad (5)$$

where $x_{new}$ is the input multivariate observation of physiological features, $x_i$ are the exemplary multivariate observations of physiological features, $x_{est}$ are the estimated multivariate observations, and K is the kernel function. In the inferential case, exemplars comprise a portion $x_i$ comprising some of the physiological features, and a portion $Y_i$ comprising the remaining features, $x_{new}$ has just the features in $x_i$, and $Y_{est}$ is the inferential estimate of those $Y_i$ features. In the autoassociative case, all features are included in $x_{new}$, $x_i$ and in the $x_{est}$ together—all estimates are also in the input.

The kernel function, by one approach, provides a similarity scalar result for the comparison of two idenfically-dimensioned observations, which:
1. Lies in a scalar range, the range being bounded at each end;
2. Has a value of one of the bounded ends, if the two vectors are identical;
3. Changes monotonically over the scalar range; and
4. Has an absolute value that increases as the two vectors approach being identical.

In one example, kernel functions may be selected from the following forms:

$$K_h(x_a, x_b) = e^{-\frac{\|x_a - x_b\|^2}{h}} \quad (6)$$

$$K_h(x_a, x_b) = \left(1 + \frac{\|x_a - x_b\|^\lambda}{h}\right)^{-1} \quad (7)$$

$$K_h(x_a, x_b) = 1 - \frac{\|x_a - x_b\|^\lambda}{h} \quad (8)$$

where $x_a$ and $x_b$ are input observations (vectors). The vector difference, or "norm", of the two vectors is used; generally this is the 2-norm, but could also be the 1-norm or p-norm. The parameter h is generally a constant that is often called the "bandwidth" of the kernel, and affects the size of the "field" over which each exemplar returns a significant result. The power λ may also be used, but can be set equal to one. It is possible to employ a different h and λ for each exemplar $x_i$. Preferably, when using kernels employing the vector difference or norm, the measured data should first be normalized to a range of 0 to 1 (or other selected range), e.g., by adding to or subtracting from all sensor values the value of the minimum reading of that sensor data set, and then dividing all results by the range for that sensor; or normalized by converting the data to zero-centered mean data with a standard deviation set to one (or some other constant). Furthermore, a kernel function according to the invention can also be defined in terms of the elements of the observations, that is, a similarity is determined in each dimension of the vectors, and those individual elemental similarities are combined in some fashion to provide an overall vector similarity. Typically, this may be as simple as averaging the elemental similarities for the kernel comparison of any two vectors x and y:

$$K(x, y) = \frac{1}{L} \sum_{m=1}^{L} K(x_m, y_m) \quad (9)$$

Then, elemental kernel functions that may be used according to the invention include, without limitation:

$$K_h(x_m, y_m) = e^{-\frac{|x_m - y_m|^2}{h}} \quad (10)$$

$$K_h(x_m, y_m) = \left(1 + \frac{|x_m - y_m|^\lambda}{h}\right)^{-1} \quad (11)$$

$$K_h(x_m, y_m) = 1 - \frac{|x_m - y_m|^\lambda}{h} \quad (12)$$

The bandwidth h may be selected in the case of elemental kernels such as those shown above, to be some kind of measure of the expected range of the $m^{th}$ parameter of the observation vectors. This could be determined, for example, by finding the difference between the maximum value and minimum value of a parameter across all exemplars. Alternatively, it can be set using domain knowledge irrespective of the data present in the exemplars or reference vectors, e.g., by setting the expected range of a heart rate parameter to be 40 to 180 beats per second on the basis of reasonable physiological expectation, and thus h equals "140" for the $m^{th}$ parameter in the model which is the heart rate.

According to one approach, Similarity-Based Modeling is used as the kernel-based multivariate estimator. Three types of SBM models can be used for human data analysis tasks: 1) a fixed SBM model, 2) a localized SBM model that localizes using a bounding constraint, and 3) a localized SBM model that localizes using a nearest neighbor approach. The fixed SBM modeling approach generates estimates using the equation below.

$$\hat{x}_{in}(t) = \frac{D(D^T \otimes D)^{-1}(D^T \otimes x_{in}(t))}{\sum (D^T \otimes D)^{-1}(D^T \otimes x_{in}(t))} \quad (13)$$

Here, D is a static m-by-n matrix of data consisting of n training data vectors with m physiological features, pre-selected from normal data during a training phase. The kernel function K is present as a kernel operator $\otimes$ whereby each column vector from the first operand (which can be a matrix, such as D is) is compared using one of the kernel functions described above, to each row vector of the second operand (which can also be a matrix). The monitored input observation is here shown as $x_{in}(t)$, and the autoassociative estimate is shown as $\hat{x}_{in}(t)$. In contrast, localized SBM (LSBM) is given by the following equation:

$$\hat{x}_{in}(t) = \frac{D(t)(D(t)^T \otimes D(t))^{-1}(D(t)^T \otimes x_{in}(t))}{\sum (D(t)^T \otimes D(t))^{-1}(D(t)^T \otimes x_{in}(t))}, \quad (14)$$

$$D(t) = \{H \mid F(H, x_{in}(t))\}$$

Although similar in form to the fixed SBM model, here the D matrix is redefined at each step in time using a localizing function F(•) based on the current input vector $x_{in}(t)$ and a normal data reference matrix H. Accordingly, matrix H contains a large set of exemplars of normal data observations, and function F selects a smaller set D using each input observation. By way of example, F can utilize a "nearest neighbor" approach to identify a set of exemplars to constitute D for the current observation as those exemplars that fall within a neighborhood of the input observation in m-dimensional space, where m is the number of features. As another example, function F can compare the input observation to the exemplars for similarity using a kernel-based comparison, and select a preselected fraction of the most similar exemplars to constitute D. Other methods of localization are contemplated by the invention, including selection on the basis of fewer than all of the physiological features, and also selection on the basis of a distinct parameter not among the features, but associated with each exemplar, such as an ambient condition measure.

Models used for estimation in the present invention are preferably empirical models determined from data, in contrast to first-principles models that relate parameters by deterministic equations. Therefore, instead of deriving a model, the model must be trained with empirical data. Training a model of physiology comprises gathering exemplary observations of the physiological parameters or features to be modeled and building a reference library of exemplars. These features can be range-normalized, or can be used in their native units of measurement in combination with an elementary kernel function, such as those shown in equations 10-12, that uses a bandwidth that is proportional to the expected range in those native units of measure. In personalized modeling, observations are obtained of the features in question from the patient who will be monitored, during conditions in which the patient is deemed to be medically normal or medically stable. The patient need not be in pristine health, as the method of the present invention looks for relative change. The normal data preferably includes representation from all manner of activity that is to be modeled, and need not be limited to highly immobile, sedated or "steady state" conditions, unless those are the only conditions that will be modeled. Exemplars are typically just observations selected for inclusion in the reference library from the larger set of available normal observations; exemplars can also be determined as computed "centers" of clustered normal data in the alternative.

Once a model is trained by constituting its reference library, and selecting the kernel function(s) that will serve as similarity operations for estimate generation, the model can be used to generate estimates responsive to monitored input observations. With each input observation, an estimate of at least some of the physiological features is generated according to one of the embodiments of equations 4, 5, 13 or 14 above. The estimated features are then differenced with the measured values of those features in the instant observation to create a residual for each such feature. Given that real-world signals have inherent measurement noise and inherent system noise, and given that empirical models will have some inherent inaccuracy, residuals will occur not only for deviating data from deteriorating physiology, but also for data from normal physiology. However the statistical character of the residuals for normal data will be much better behaved than for deviating data. A number of well known methods for testing raw data can be applied to the residuals, including thresholds. A threshold can be applied to a residual such that small variations are tolerated, by larger values trigger an alert. Series of decisions on residuals for individual physiological parameters can be the basis for rules relating to the genuine existence of a persistent deviating health condition, for example by counting the number of threshold exceedances in a window of observations. Rule patterns can be applied across residuals for different physiological features, triggered only when the pattern of deviations in the residuals is identified. Generally, these decision methods applied to residuals are more sensitive and less prone to error than the same approaches applied to raw data, because normal variation has been removed in the residuals by the differencing with the estimated features from the model. Essentially, SBM is removing the normal variation in the actual data and leaving behind abnormal data in the form of residuals (normal as defined by the training data).

Figure 6:
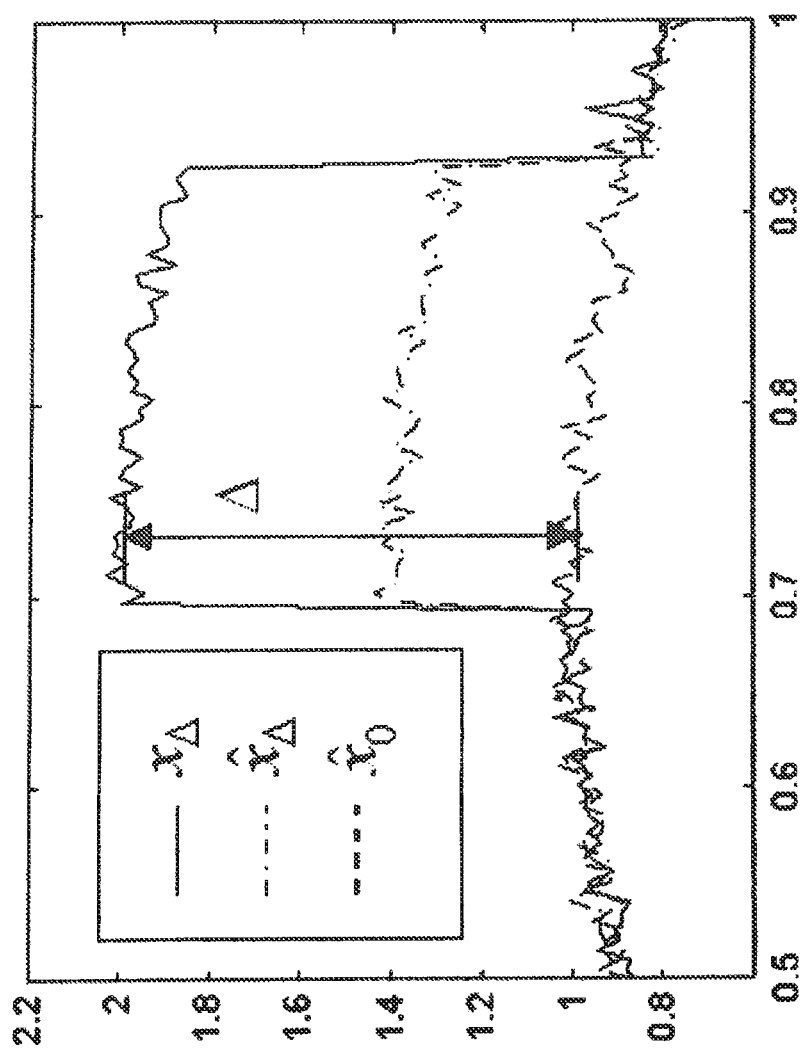
FIG. 6 is a plot of an exemplary physiological feature time series showing perturbations of that time series used in accuracy and robustness calculations.

The performance of a model can be measured using a nonparametric perturbation-based approach that is particularly well suited for comparing modeling techniques used for anomaly detection applications. The performance of a model is assessed using three metrics: 1) robustness, 2) spillover and 3) error. The robustness metric is a measurement of the likelihood that a model will follow (or over-fit) a perturbation introduced into the data. With reference to FIG. 6, to measure robustness, first estimates for all of the variables in a model are made based on a test data set containing normal data ($\hat{x}_0$ in FIG. 6). Next, a perturbation $\Delta$ is added to each variable one at a time in the model as shown ($x_\Delta$ in FIG. 6). Finally, estimates are generated for each of the perturbed variables ($\hat{x}_\Delta$ in FIG. 6). The robustness metric for each variable in a model is then given by the following equation:

$$\text{Robustness} = \frac{\text{mean}(|\hat{x}_0 - \hat{x}_\Delta|)}{\Delta} \quad (15)$$

Here, perfect robustness is achieved when Robustness is equal to 0, that is, when the unperturbed and perturbed estimates are identical. A larger value indicates more over-fitting and hence less model robustness.

The spillover metric measures the relative amount that variables in a model deviate from normality when another variable is perturbed. In contrast to robustness, spillover measures the robustness on all other variables when one variable is perturbed. The spillover measurement for each variable is calculated using a similar calculation, which is given by $$Spillover_j = \frac{1}{M-1} \sum_{i=1, i \neq j}^{M} \frac{\text{mean}(|\hat{x}_{i0} - \hat{x}_{i|\Delta_j}|)}{\Delta_i} \quad (16)$$

where $\hat{x}_{i0}$ is the estimate for variable i when no variables are perturbed, is the estimate of variable i when variable j is perturbed by $\Delta_j$, and $\Delta i$ is the perturbation amount used when variable i is itself perturbed.

Finally, the error metric is simply the root mean squared error of the difference between the actual value and its estimate divided by the standard deviation of the actual value, or equivalently the residual RMS divided by the actual value standard deviation:

$$Error = \frac{\text{rms}(x - \hat{x})}{\sigma_x} \equiv \frac{\text{rms}(\text{residual})}{\sigma_x} \quad (17)$$

The equations listed above define the metrics for each variable in a model. In each case, a smaller value is better. The overall performance metrics for a model are calculated by averaging the results for each variable in each case.

Turning to one form of residual testing, a multivariate density estimation approach can be applied to the residual data. The approximated densities in the normal behavior of the data are used to determine the likelihood (in the form of a multivariate health index (MHI)) that a new data point is part of the normal behavior distribution. The density estimates are calculated using a non-parametric kernel estimator with a Gaussian kernel. The estimator is shown in the equation below. The resulting density function is essentially a mixture of N individual multivariate Gaussian functions each centered at $x_i$:

$$\hat{f}(x) = \frac{1}{N(2\pi)^{d/2} h^d} \sum_{i=1}^{N} \exp\left[-\frac{1}{2} \frac{\|x - x_i\|}{h^2}\right] \quad (18)$$

where N is the number of training vectors, h is a bandwidth parameter, d is the dimensionality of the vectors, and $\hat{f}(x)$ is a scalar likelihood. Importantly, the x and $x_i$ here are not multivariate observations of physiological features, but are instead multivariate residual observations derived from the original observations by differencing with the estimates. Importantly also, the density "estimation" here is not the same as the estimation process described above for estimating physiological feature values based on measured values; the "estimate" here is empirically mapping out a probability distribution for residuals using the normal multivariate residual exemplars, as a Gaussian mixture model. This estimated distribution is then used to compute a likelihood that a new multivariate residual from an input observation of physiological features is a member of that distribution or not. The exemplars $x_i$ can be selected from regions of normal data residuals generated by SBM using test data that is deemed "normal" or representative of desired or stable physiological behavior. Before the density estimates are made, all residuals are scaled to have unit variance and zero mean, or at least are scaled to have unit variance. The means and standard deviations used for the scaling procedure are calculated from known normal data residuals. The multivariate health index (MHI) in one form is a function of $\hat{f}(x)$ and is given by:

$$MHI(x) = \log_{10}\left(\frac{1}{\hat{f}(x)}\right) \quad (19)$$

Of course, the likelihood determined from equation 18 need not be converted as in equation 19 in order to be useful, and equation 19 is used primarily to invert the signal trend (so that higher equates to rising health risk). Tests may be applied directly to the result of equation 18.

A comparison of the efficacy of applying the multivariate density estimation approach to residuals is highlighted in FIGS. 7A-7B. Chart 705 (FIG. 7A) shows a multivariate density estimation similar to that described above except applied to raw physiological feature data (the actual values of heart rate, respiration rate, etc.); while chart 710 (FIG. 7B) shows the multivariate density estimation as described above applied to residuals generated from a kernel-based model (SBM). MHI results are shown for physiological data both unperturbed (normal) and with an artificially-induced perturbation (abnormal). The perturbation was introduced as a slow drift in a subset of ambulatory physiological features from the start of the data, with a maximum drift achieved at the end of the data. In both chart 705 and 710, the MHI computed for "normal" unperturbed data is shown as a solid line, and the MHI computed for "abnormal" perturbed data is shown as a dotted line. A detection threshold (717, 720) was determined for each approach based on statistics for a test set of normal data, where the statistics were for raw data in the case of chart 705 and for residuals in the case of chart 710. A decision algorithm was further applied to the MHI to ascertain a persistent, reliable threshold exceedance alert, in this case x successive MHI threshold exceedances yields an alert decision. The decision can be latched until a series of y successive values for MHI are observed below the threshold, in which case the alert is removed. Alternatively, an alert can be latched when there have been x threshold exceedances in a window of m observations, and the alert removed when there have been y observations below the threshold in a window of b observations. In each case, the vertical line (730, 735) indicates the point at which a decision was made that the data are not from the normal behavior distribution and hence indicate an abnormal condition. As can be seen, detection occurs about one-third of the way from the start of the simulated disturbance for the residual-driven MHI, whereas detection using raw data in combination with a multivariate density estimation does not occur until much later in the data. This is due to the combination of a model of normalcy removing normal variation, with the multivariate density estimation of likelihood of normalcy applied to residuals. This residual-based MHI method has the novel advantages of providing substantially earlier detection of an incipient pattern of deviation in health, and providing a single index of patient deviation to summarize individual residuals for the multiple physiological features being monitored.

According to one approach, the system described herein can be deployed to provide predictive monitoring of patient health in an ambulatory, at-home environment, particularly for patients with chronic diseases that may deteriorate unpredictably. Multiple physiological features are derived from one or more biosignals and parameters captured from a wearable or implanted device (or both), and transmitted to an analytics data center, where one or more servers are disposed to process the physiological features using empirical, kernel-based models. The models are preferably personalized to the data from the patient captured during periods when the patient is considered to be in normal or acceptably stable health, to provide a model of normal physiology for the patient. Monitored data is estimated using the personalized model, and the monitored values are differenced with the estimated values of the physiological parameters to yield residuals. The residuals are then processed through one or more methods of analysis to yield alerts regarding the patient's health status. According to one technique, the residuals can individually be tested with rules, such as thresholds. These thresholds can further be tested for persistence. Patterns of residual tests can be recognized to yield even more specific health status information. According to another technique, the multivariate observation of residuals can be examined for likelihood of belonging to a "normal" residual distribution using an empirical multivariate probability density estimation, and this likelihood may then be converted to a multivariate health index, typically as an inverse log value of the likelihood. The MHI provides an instant ranking of patient health status, and the MHI can be tested using a threshold, as well as persistence rules, to yield alerts regarding patient health status. All such analytics can be presented via a web-based or client-server-based user interface to medical practitioners, and in this way a large population of patients can be monitored together by medical staff with improved efficiency. All such monitored patients of a health care institution or practice group can be managed for early warning of deteriorating health at home, and the patients can be prioritized for specific follow-up based on health status. Patients with early indications of health deterioration can be contacted to verify compliance with medications, inquire about how the patient feels, and investigate recent patient behavior that may have exacerbated a chronic illness. Medical staff may advantageously avert a more costly health emergency for the patient with efficient interventions including instructing the patient to make adjustments to medications, comply with medications, or come in for an examination and preventative intervention.

SBM can also be deployed with cross subject modeling, instead of an entirely personalized model. A model then comprises data from other human subjects. Due to the person to person variation in feature data it is necessary to scale each subject's data. A generic cross population model can be used as a temporary means for monitoring a human when no historical data are available for the individual as long as the individual's feature data are properly scaled. The scaling can be accomplished based on statistics calculated during a standardized set of activities when the monitoring device is first put on. The data acquired during the standard activities (which can comprise lying down, sitting, standing, walking and climbing stairs, for example) is typically scaled to a zero-mean, one-standard deviation range. The monitoring is not as sensitive as it would be for a personalized model but it at least provides a minimal level of health monitoring while waiting to acquire a suitable set of data to generate a personalized model.

Figure 8:
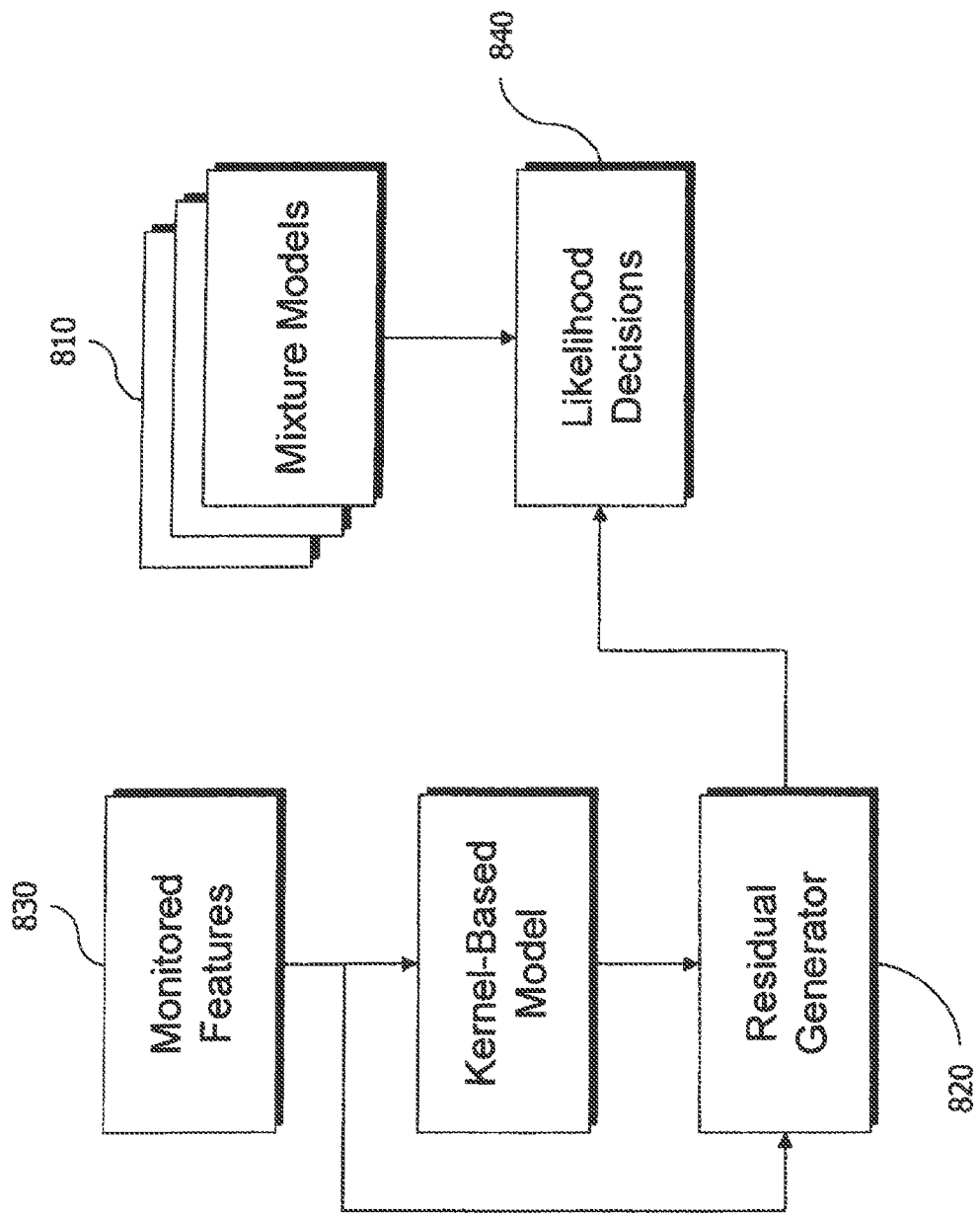
FIG. 8 is a block diagram showing an alternative embodiment.

Turning to FIG. 8, another approach obtains residuals from reference data representative of a known illness, malady or health deterioration, so that a multivariate probability density estimator can be determined for that health deterioration, in contrast to determining it for normal or stable health. Hence, one or more probability density estimators 810 can be created in this way (including one for normal data), and applied to multivariate residual observations 820 from monitored data 830. Likelihoods that the monitored residual observation belongs to each of the distributions can be compared in parallel in a decisioning step 840, and not only can deviation from normal be detected, but the nature of the health deterioration can be categorized. Likelihoods can simply be displayed to medical staff, or the likeliest scenario or the set of scenarios with a sufficiently high likelihood can be indicated as the probable state(s) of the patient in 840. In another approach to decisioning 840, the likelihoods or MHI values for each of a plurality of maladies are normalized using test statistics generated from known examples of each such malady processed through model estimation and residual generation, so that they can be expressed in terms of the typical variance expected for residual vectors fitting each such category. Then the normalized values are compared to determine which category is in fact most likely represented by the current monitored data. Series of MHI or likelihood values for each malady category can also be processed heuristically to rank categories, for example with moving window averages or medians.

According to another form, patients in a hospital are monitored with multivariate physiological parameters derived from sensors using conventional bedside monitors, ventilators, and/or wearable or implanted devices. Data is streamed via Ethernet network or WiFi to a central station/nursing station or to a hospital centralized data center, coupled to interfaces for medical staff real-time monitoring. Data is also streamed via. Ethernet network or WiFi to analytics server(s) for processing using empirical, kernel-based models as described herein. Estimates are made of the physiological features, and residuals are generated; models may be generic instead of personalized, since no personal data may be available for a patient from a period when that patient was in acceptable physiological health. In such a case, a model can comprise data from other humans collected in similar hospital conditions when the humans were in acceptable health. Such a model can further be tailored to the monitored patient on the basis of major contributors to normal physiological variation, such as body mass, gender, age, and medical condition (e.g., similar cardiac ejection fraction or similar respiratory performance). Residuals are processed as described above to generate MHI and/or rules-based decisions. Patient health status for all monitored patients in the ward or hospital or ICU can be monitored by onsite medical staff or off-site medical staff to provide early warning of developing health issues, such as infection, pneumonia, and sepsis.

With the advantage of early warning as provided by the invention, the health alerts of patients can be managed in a proactive manner, rather than being a crisis that must be immediately responded to. The user interface provides for several levels of alert management: Alerts can be dismissed (investigation by medical staff shows the alert to be anomalous); alerts can be confirmed and elevated (investigation by medical staff shows a definite health issue is present that needs intervention); and alerts can be marked for further follow-up and observation (investigation shows close monitoring is warranted but immediate intervention is not required or advised).

A system is provided for advanced warning of health problems, using a wearable sensing device for capturing rich physiological data streams from a human outside the hospital, in the daily routine of their home life, providing high visibility into a patient's physiological status outside the reach of the physician's office or the hospital ward. Automated processing of this data using algorithms that remove the normal variation present in ambulatory data, to provide robust and early detection of anomalies indicative of incipient health issues is novel and inventive. The potential for this combination of device plus algorithm to revolutionize patient care is enormous, especially for the chronically ill patient population. This platform is exactly the kind of tool needed by physicians to improve patient outcomes, avoid unnecessary costs, and greatly extend the leverage of the medical workforce.

It will be appreciated by those skilled in the art that modifications to the foregoing preferred embodiments may be made in various aspects and as set forth with particularity in the appended claims. It is deemed that the spirit and scope of the invention encompasses such modifications and alterations to the preferred embodiment as would be apparent to one of ordinary skill in the art and familiar with the teachings of the present application.

What is claimed is:

1. A method for monitoring the health of a human, comprising:
    obtaining sensor data from a human;
    generating with a programmed microprocessor a plurality of features from said sensor data, characteristic of physiological health of said human;
    estimating with a programmed microprocessor values for said features characteristic of normal human physiology using a multivariate model, based on the values of said generated plurality of features;
    differencing with a programmed microprocessor the estimated values and the generated features to provide a set of residuals for the features, wherein each residual is the difference between the particular feature value expected according to said model, and the corresponding feature value generated from said sensor data; and
    determining with a programmed microprocessor a likelihood that said set of residuals is representative of a pattern of normal residuals, by using a Gaussian mixture model based on a set of normal residual reference patterns to approximate a probability distribution for normal residual patterns, and to compute said likelihood that said set of residuals belongs to the distribution, whereby said likelihood consolidates the behaviors of the individual residuals for each of the features into one overall index; and
    applying with a programmed microprocessor a test to said likelihood to render a decision whether the generated features are characteristic of normal physiological behavior to provide an early indication of deviation of the physiological health of said human from normal.

2. A method according to claim 1, wherein said step of applying a test comprises comparing with a programmed microprocessor the logarithm of the inverse of said likelihood to a threshold.

3. A method according to claim 1, further comprising the step of
    testing with a programmed microprocessor a series of said rendered decisions for persistence of like decisions.

4. A method according to claim 1, wherein said step of estimating values further comprises making a kernel-based comparison of a feature vector, comprising the values of said feature signals, to at least some of a library of exemplary vectors, each comprising values representative of said feature signals in a known health state, in order to generate said estimate as a linear combination of those exemplary vectors, weighted in relation to said comparisons.

5. A method according to claim 4, wherein said feature vector is compared to said exemplary vectors comprising said library in order to select a subset of said exemplary vectors to use in said kernel-based comparison for generating said estimate.

6. A method according to claim 4, wherein said estimate is generated as a linear combination of said exemplary vectors, weighted in relation to said comparisons according to:

$$x_{est} = \frac{\sum_{i=1}^{L} x_i K(x_{new}, x_i)}{\sum_{i=1}^{L} K(x_{new}, x_i)}$$

where $x_{new}$ is said feature vector, $x_i$ are said exemplary vectors, $x_{est}$ is said estimate, and K is said kernel-based comparison.

7. A method according to claim 4, wherein said estimate is generated as a linear combination of said exemplary vectors, weighted in relation to said comparisons according to:

$$x_{est} = \frac{D(D^T \otimes D)^{-1}(D^T \otimes x_{new})}{\sum (D^T \otimes D)^{-1}(D^T \otimes x_{new})}$$

where $x_{new}$ is said feature vector, D is a matrix of at least some of said exemplary vectors, $x_{est}$ is said estimate, and $\hat{x}$ is an operator for performing said kernel-based comparisons between matrices.

8. A method according to claim 4, wherein said kernel-based comparison is of the form:

$$K_h(x_a, x_b) \propto e^{-\frac{\|x_a - x_b\|_p^n}{h}}$$

where $x_a$ and $x_b$ are vectors being compared, h is a constant, p is the order of the norm, and n is a power to which the norm is raised, and K is the scalar result of the comparison.

9. A method according to claim 4, wherein said kernel-based comparison is of the form:

$$K_h(x_a, x_b) \propto \left(1 + \frac{\|x_a - x_b\|_p^n}{h}\right)^{-1}$$

where $x_a$ and $x_b$ are vectors being compared, h is a constant, p is the order of the norm, and n is a power to which the norm is raised, and K is the scalar result of the comparison.

10. A method according to claim 4, wherein said kernel-based comparison is of the form:

$$K_h(x_a, x_b) \propto 1 - \frac{\|x_a - x_b\|_p^n}{h}$$

where $x_a$ and $x_b$ are vectors being compared, h is a constant, p is the order of the norm, and n is a power to which the norm is raised, and K is the scalar result of the comparison.

11. A method according to claim 4, wherein said kernel-based comparison is of the form:

$$K(x, y) \propto \frac{1}{L} \sum_{m=1}^{L} e^{\frac{-|x_m - y_m|^n}{h_m}}$$

where x and y are vectors being compared, $h_m$ are constants, m is the number of features, and n is a constant power, and K is the scalar result of the comparison.

12. A method according to claim 4, wherein said kernel-based comparison is of the form:

$$K(x, y) \propto \frac{1}{L} \sum_{m=1}^{L} \left(1 + \frac{|x_m - y_m|^n}{h_m}\right)^{-1}$$

where x and y are vectors being compared, $h_m$ are constants, m is the number of features, and n is a constant power, and K is the scalar result of the comparison.

13. A method according to claim 4, wherein said kernel-based comparison is of the form:

$$K(x, y) \propto \frac{1}{L} \sum_{m=1}^{L} \left(1 - \frac{|x_m - y_m|^n}{h_m}\right)$$

where x and y are vectors being compared, $h_m$ are constants, m is the number of features, and n is a constant power, and K is the scalar result of the comparison.

14. A method according to claim 1, wherein said step of obtaining sensor data comprises making measurements of sensors embedded inside the monitored human in connection with an implanted cardiac device.

15. A method according to claim 1, wherein said step of obtaining sensor data comprises receiving wireless transmissions via extremely local radio protocol of measurements of sensors attached to the monitored human.

16. A method according to claim 1, wherein said step of obtaining sensor data comprises receiving data from a ventilator.

17. A method for monitoring the health of a human, comprising:
obtaining sensor data from a human;
generating with a programmed microprocessor a plurality of features from said sensor data, characteristic of physiological health of said human;
estimating with a programmed microprocessor values for said features characteristic of normal human physiology using a multivariate model, based on the values of said generated plurality of features;
differencing with a programmed microprocessor the estimated values and the generated features to provide a set of residuals for the features, wherein each residual is the difference between the particular feature value expected according to said model, and the corresponding feature value generated from said sensor data;
determining with a programmed microprocessor for each of a plurality of known health states, a likelihood that said set of residuals is representative of a pattern of residuals characteristic of that known health state, by using a Gaussian mixture model based on a set of residual reference patterns for the known health state to approximate a probability distribution for residual patterns of that known health state, and to compute said likelihood that said set of residuals belongs to the distribution; and
applying with a programmed microprocessor a test to the plurality of likelihoods, each corresponding to one of the known health states, to render a ranking of which of said plurality of known health states the generated features are most characteristic of.

18. A method according to claim 17, wherein said step of estimating values further comprises making a kernel-based comparison of a feature vector, comprising the values of said feature signals, to at least some of a library of exemplary vectors, each comprising values representative of said feature signals in a known health state, in order to generate said estimate as a linear combination of those exemplary vectors, weighted in relation to said comparisons.

19. A method according to claim 18, wherein said feature vector is compared to said exemplary vectors comprising said library in order to select a subset of said exemplary vectors to use in said kernel-based comparison for generating said estimate.

20. A method according to claim 18, wherein said estimate is generated as a linear combination of said exemplary vectors, weighted in relation to said comparisons according to:

$$x_{est} = \frac{\sum_{i=1}^{L} x_i K(x_{new}, x_i)}{\sum_{i=1}^{L} K(x_{new}, x_i)}$$

where $x_{new}$ is said feature vector, $x_i$ are said exemplary vectors, $x_{est}$ is said estimate, and K is said kernel-based comparison.

21. A method according to claim 18, wherein said estimate is generated as a linear combination of said exemplary vectors, weighted in relation to said comparisons according to:

$$x_{est} = \frac{D(D^T \otimes D)^{-1}(D^T \otimes x_{new})}{\sum (D^T \otimes D)^{-1}(D^T \otimes x_{new})}$$

where $x_{new}$ is said feature vector, D is a matrix of at least some of said exemplary vectors, $x_{est}$ is said estimate, and $\hat{x}$ is an operator for performing said kernel-based comparisons between matrices.

22. A method according to claim 1, wherein the sensor data of said receiving step comprises an electrocardiogram, a bioimpedance, and a photoplethysmogram for at least two wavelengths.

23. A method according to claim 22, wherein the plurality of features of said generating step comprises a heart rate, a respiration rate, a pulse transit time, and a ratio of absorption of the at least two wavelengths.

24. A method according to claim 23, wherein the sensor data of said receiving step further comprises at least one accelerometer signal, and further comprising the step of identifying what times the accelerometer signal indicates motion artifact is likely present in the sensor data and ignoring sensor data at those times.

25. A method according to claim 1, wherein said step of determining a likelihood further comprises scaling said residuals for the generated features, using the means and standard deviations calculated from known normal data residuals, and wherein said set of normal residual reference patterns are likewise scaled.

26. A method according to claim 3, wherein said step of testing a series of rendered decisions comprises toggling on an alert latch when there have been a first selected minimum count of rendered decisions, within a first selected window of successive observations of the generated features, that the features are not characteristic of normal physiological behavior.

27. A method according to claim 26, wherein said step of a testing series of rendered decisions further comprises, once the alert latch is on, toggling off the alert latch when there have been a second selected minimum count of rendered decisions, within a second selected window of successive observations of the generated features, that the features are characteristic of normal physiological behavior.

28. A method according to claim 17, wherein the sensor data of said receiving step comprises an electrocardiogram, a bioimpedance, and a photoplethysmogram for at least two wavelengths.

29. A method according to claim 28, wherein the plurality of features of said generating step comprises a heart rate, a respiration rate, a pulse transit time, and a ratio of absorption of the at least two wavelengths.

30. A method according to claim 29, wherein the sensor data of said receiving step further comprises at least one accelerometer signal, and further comprising the step of identifying what times the accelerometer signal indicates motion artifact is likely present in the sensor data and ignoring sensor data at those times.

31. A method according to claim 17, wherein said step of determining, for each of a plurality of known health states, a likelihood further comprises scaling said residuals for the generated features, using the means and standard deviations calculated from known normal data residuals for each respective known health state, and wherein said set of normal residual reference patterns are likewise scaled.

* * * * *